United States Patent
Xiao et al.

(10) Patent No.: US 11,955,240 B1
(45) Date of Patent: Apr. 9, 2024

(54) NEURAL-NETWORK-BASED-IMPLEMENTED OPHTHALMOLOGIC INTELLIGENT CONSULTATION METHOD AND APPARATUS

(71) Applicant: Renmin Hospital of Wuhan University (Hubei General Hospital), Hubei (CN)

(72) Inventors: Xuan Xiao, Hubei (CN); Xiang Gao, Hubei (CN); Ting Chen, Hubei (CN); Ting Su, Hubei (CN); Xuejie Li, Hubei (CN)

(73) Assignee: Renmin Hospital of Wuhan University (Hubei General Hospital), Hubei (CN)

( * ) Notice: Subject to any disclaimer, the term of this patent is extended or adjusted under 35 U.S.C. 154(b) by 0 days.

(21) Appl. No.: 18/465,977

(22) Filed: Sep. 12, 2023

(30) Foreign Application Priority Data

Apr. 14, 2023 (CN) .......................... 202310395603.5

(51) Int. Cl.
*G06T 7/00* (2017.01)
*A61B 3/00* (2006.01)
(Continued)

(52) U.S. Cl.
CPC ........... *G16H 50/20* (2018.01); *A61B 3/0025* (2013.01); *A61B 3/14* (2013.01); *A61B 5/4803* (2013.01);
(Continued)

(58) Field of Classification Search
None
See application file for complete search history.

(56) References Cited

U.S. PATENT DOCUMENTS

| 10,430,946 B1 | 10/2019 | Zhou et al. |
| 2008/0044063 A1 | 2/2008 | Friedman et al. |

(Continued)

FOREIGN PATENT DOCUMENTS

| CN | 104637031 | 5/2015 |
| CN | 108091393 | 5/2018 |

(Continued)

OTHER PUBLICATIONS

Das, Anthony Vipin, et al. "App-based tele ophthalmology: a novel method of rural eye care delivery connecting tertiary eye care center and vision centers in India." International Journal of Telemedicine and Applications 2019 (2019). (Year: 2019).*

(Continued)

*Primary Examiner* — Samah A Beg
(74) *Attorney, Agent, or Firm* — JCIP GLOBAL INC.

(57) ABSTRACT

A neural-network-based-implemented ophthalmologic intelligent consultation method includes: performing correction filtering on a consultation voice of a patient, framing the voice into a consultation voice frame sequence, generating a consultation text corresponding to the consultation voice frame sequence based on phoneme recognition and phoneme transcoding, and extracting an ophthalmologically-described disease; performing gray-level filtering, primary picture segmentation, and size equalization operation on an eye picture set of the to-be-diagnosed patient to acquire a standard eyeball picture group; extracting eye white features, pupil features and blood vessel features from the standard eyeball picture group, performing lesion feature analysis on the eye white features, the pupil features and the blood vessel features to acquire an ophthalmologically-observed disease, and based on the ophthalmologically-observed disease and the ophthalmologically-described disease, generating a consultation result.

9 Claims, 3 Drawing Sheets

(51) Int. Cl.
  *A61B 3/14* (2006.01)
  *A61B 5/00* (2006.01)
  *G06T 5/30* (2006.01)
  *G06T 5/40* (2006.01)
  *G06T 7/12* (2017.01)
  *G06V 10/77* (2022.01)
  *G06V 10/82* (2022.01)
  *G06V 20/70* (2022.01)
  *G10L 15/02* (2006.01)
  *G10L 15/05* (2013.01)
  *G10L 15/16* (2006.01)
  *G10L 15/18* (2013.01)
  *G10L 15/22* (2006.01)
  *G10L 21/0224* (2013.01)
  *G10L 25/18* (2013.01)
  *G10L 25/21* (2013.01)
  *G16H 50/20* (2018.01)

(52) U.S. Cl.
  CPC .............. *G06T 5/30* (2013.01); *G06T 5/40* (2013.01); *G06T 7/0012* (2013.01); *G06T 7/12* (2017.01); *G06V 10/7715* (2022.01); *G06V 10/82* (2022.01); *G06V 20/70* (2022.01); *G10L 15/02* (2013.01); *G10L 15/05* (2013.01); *G10L 15/16* (2013.01); *G10L 15/1815* (2013.01); *G10L 15/22* (2013.01); *G10L 21/0224* (2013.01); *G10L 25/18* (2013.01); *G10L 25/21* (2013.01); *G06T 2207/20084* (2013.01); *G06T 2207/30041* (2013.01); *G06T 2207/30096* (2013.01); *G06T 2207/30101* (2013.01); *G06V 2201/03* (2022.01); *G10L 2015/025* (2013.01)

(56) References Cited

U.S. PATENT DOCUMENTS

| | | | |
|---|---|---|---|
| 2008/0198328 A1* | 8/2008 | Seriani | A61B 3/0025 |
| | | | 351/205 |
| 2008/0253622 A1 | 10/2008 | Tosa et al. | |
| 2015/0055094 A1 | 2/2015 | Boate et al. | |
| 2018/0070818 A1 | 3/2018 | Sakai | |
| 2018/0322254 A1* | 11/2018 | Smurro | H04N 21/23614 |
| 2023/0074869 A1 | 3/2023 | Sun | |

FOREIGN PATENT DOCUMENTS

| | | |
|---|---|---|
| CN | 108198620 | 6/2018 |
| CN | 110022753 | 7/2019 |
| CN | 110335266 | 10/2019 |
| CN | 111667490 | 9/2020 |
| CN | 112233087 | 1/2021 |
| CN | 112513999 | 3/2021 |
| CN | 113488200 | 10/2021 |
| CN | 113962311 | 1/2022 |
| CN | 114140437 | 3/2022 |
| CN | 114388145 | 4/2022 |
| CN | 114582008 | 6/2022 |
| CN | 114996463 | 9/2022 |
| CN | 115512698 | 12/2022 |
| EP | 3449810 | 3/2019 |
| JP | 2007125151 | 5/2007 |
| WO | 2017173478 | 10/2017 |
| WO | 2019180742 | 9/2019 |
| WO | 2023029510 | 3/2023 |

OTHER PUBLICATIONS

Li, Ji-Peng Olivia, et al. "Digital technology, tele-medicine and artificial intelligence in ophthalmology: A global perspective." Progress in retinal and eye research 82 (2021): 100900. (Year: 2021).*
"Search Report of China Counterpart Application", dated May 10, 2023, with English translation thereof, p. 1-p. 9.
"Search Report of China Counterpart Application", dated May 19, 2023, with English translation thereof, p. 1-p. 8.
Lv, Xiangyun; et al., "Optical coherence tomography angiography (OCTA) was used to observe the macular blood flow after rhegmatogenous retinal detachment reduction," Rec Adv Ophthalmol., vol. 38, No. 12, with English translation thereof, Dec. 2018, pp. 1-8.
Yuan, Weiqi; et al., "Corneal senile ring segmentation based on multi-scale color replacement," Chinese Journal of Scientific Instrument, vol. 38, No. 1, with English translation thereof, Jan. 2017, pp. 1-18.
Liu, Dongxu, "Research on Eye Image Recognition Algorithm Based on Watershed Segmentation and Color Depth Features," Journal of changchun institute of technology (Natural Science Edition), vol. 22, No. 3, with English translation thereof, Mar. 2021, pp. 1-10.
Tomoki Hayashi; et al., "Multi-Head Decoder for End-to-End Speech Recognition," arXiv:1804.08050v2 [cs.CL], Jul. 2018, pp. 1-5.
Xiangyu Chen; et al., "Multiple Ocular Diseases Classification with Graph Regularized Probabilistic Multi-label Learning," Computer Vision—ACCV 2014, 12th Asian Conference on Computer Vision Singapore, Nov. 2014 Revised Selected Papers, Part IV, pp. 127-142.
M. Prashasthi; et al., "Image Processing Approach to Diagnose Eye Diseases," Intelligent Information and Database Systems, 9th Asian Conference, ACIIDS 2017, Kanazawa, Japan, Apr. 2017 Proceedings, Part II, pp. 245-254.
Manjulasri Rayudu; et al., "Review of Image Processing Techniques for Automatic Detection of Eye Diseases," 2012 Sixth International Conference on Sensing Technology (ICST), Dec. 2012, pp. 1-6.
Wu, Xiaohang; et al., "Analysis of the effect of ophthalmic Internet AI diagnosis and treatment services during the COVID-19 outbreak," China Digital Medicine, vol. 15, Issue 9, with English translation thereof, Sep. 2020, pp. 1-19.
Gao, Ming Hui; et al., "Preliminary analysis and application of the network consultation platform based on artificial intelligence," Wireless Internet technology, vol. 17, Issue 9, with English translation thereof, May 2020, pp. 1-8.

* cited by examiner

NEURAL-NETWORK-BASED-IMPLEMENTED OPHTHALMOLOGIC INTELLIGENT CONSULTATION METHOD AND APPARATUS

CROSS-REFERENCE TO RELATED APPLICATION

This application claims the priority benefit of China application serial no. 202310395603.5, filed on Apr. 14, 2023. The entirety of the above-mentioned patent application is hereby incorporated by reference herein and made a part of this specification.

TECHNICAL FIELD

The present disclosure relates to the field of artificial intelligence technologies, and in particular to a neural-network-based-implemented ophthalmologic intelligent consultation method and apparatus.

BACKGROUND

Information of the World Health Organization shows that ophthalmic disease including refractive error has become a third largest disease threatening human health and living quality, following the tumor and the cardio-cerebrovascular distortion. As the number of the ophthalmic patients increases, the ophthalmologists have increasingly more work load. A neural-network-based intelligent consultation system can assist the ophthalmologists in determining the diseases and increasing the consultation efficiency.

Most of the existing neural-network-based ophthalmologic consultation methods are based on simple eye picture recognition and classification. For example, feature extraction is performed on an eye picture of a patient, and based on the extracted features, a lesion is located and the type of the lesion is identified. In practical applications, the consultation method based on simple eye picture recognition and classification requires a large number of eye pictures of different features for training in order to acquire a high disease identification rate. Due to different positions of the lesions and different sizes of the diseases of the patients, the identification rate for the diseases will be reduced significantly, further leading to a lower accuracy in the ophthalmologic intelligent consultation process.

SUMMARY

The present disclosure provides a neural-network-based-implemented ophthalmologic intelligent consultation method and apparatus, which aims to address the problem of the low accuracy in the ophthalmologic intelligent consultation process.

In order to realize the above purpose, the present disclosure provides a neural-network-based-implemented ophthalmologic intelligent consultation method, which includes:

acquiring a consultation voice of a to-be-diagnosed patient, performing correction filtering on the consultation voice to acquire a filtered voice, framing the filtered voice into a consultation voice frame sequence, and extracting voice features for the voice frames to acquire a consultation voice feature sequence, wherein framing the filtered voice into the consultation voice frame sequence comprises:

performing primary framing on the filtered voice based on a preset framing window length to acquire a framed voice sequence;

based on the following mainlobe windowing algorithm, performing windowing processing on the framed voice sequence to acquire a windowed voice sequence:

$$H(w) = \left\{ 0.5A(w) + 0.25\left[ A\left(w - \frac{2\pi}{N-1}\right) + A\left(w + \frac{2\pi}{N-1}\right) \right] \right\} e^{-jw(N-1)/2}$$

wherein H(w) refers to a frequency value of the w-th windowed voice in the windowed voice sequence, A(w) refers to a frequency value of the w-th framed voice in the framed voice sequence, π is a symbol of Pi, N refers to a voice window length corresponding to the mainlobe windowing algorithm, e is a symbol of an Euler number, and j is a symbol of an imaginary number;

calculating an average zero-crossing rate and a short-time voice energy of the windowed voice sequence, and performing endpoint detection on the windowed voice sequence based on the average zero-crossing rate and the short-time voice energy to acquire the consultation voice frame sequence;

performing phoneme recognition on the voice feature sequence to acquire a consultation phoneme sequence, transcoding, by a self-attention, the phoneme sequence into a consultation text, performing text segmentation and vectorization operation on the consultation text sequentially to acquire consultation text features, and performing semantics recognition on the consultation text features to acquire an ophthalmologically-described disease;

acquiring an eye picture set of the to-be-diagnosed patient, screening out a sharp eye picture group from the eye picture set, performing gray-level filtering operation on the sharp eye picture group to acquire a filtered eye picture group, and performing primary picture segmentation and size equalization operations on each filtered eye picture in the filtered eye picture group to acquire a standard eyeball picture group;

performing secondary picture segmentation operation on the standard eyeball picture group to acquire an eye white picture group, a pupil picture group, and a blood vessel picture group, and extracting eye white features from the eye white picture group, pupil features from the pupil picture group and blood vessel features from the blood vessel picture group; performing lesion feature analysis on the eye white features, the pupil features and the blood vessel features to acquire an ophthalmologically-observed disease, and generating a consultation result based on the ophthalmologically-observed disease and the ophthalmologically-described disease.

Optional, performing correction filtering on the consultation voice to acquire the filtered voice comprises:

performing array signal transformation on the consultation voice to acquire a consultation array signal, and based on the consultation array signal, generating a time sequence of the consultation voice;

based on the consultation array signal and the time sequence, generating a voice trend term of the consultation voice, and based on the voice trend term, performing voice correction on the consultation array signal to acquire a corrected voice;

performing denoising and filtering on the corrected voice to acquire a filtered voice.

Optional, extracting voice features for the voice frames to acquire a consultation voice feature sequence comprises:
performing fast discrete Fourier Transform on the consultation voice feature sequence to acquire a consultation voice spectrum sequence;
performing Mel filtering on the consultation voice spectrum sequence to acquire a consultation Mel spectrum sequence;
performing log inverse transform on the consultation Mel spectrum sequence to acquire a consultation voice feature sequence.

Optional, performing phoneme recognition on the voice feature sequence to acquire the consultation phoneme sequence comprises:
adding position features to the voice feature sequence to acquire voice feature codes;
generating a multi-head voice code vector set of the voice feature codes, and based on self-attention mechanism, calculating morpheme attention features corresponding to the multi-head voice code vector set;
performing attention decoding on the morpheme attention features to acquire a consultation phoneme sequence.

Optional, transcoding, by the self-attention, the phoneme sequence into the consultation text comprises:
based on a pre-trained self-attention model, performing primary decoding on the phoneme sequence to acquire a consultation candidate word set sequence;
based on the consultation candidate word set sequence, generating a candidate word sequence, selecting each candidate word in the candidate word sequence as target candidate word, and based on a pre-trained semantics network, generating a following word set corresponding to the target candidate word;
based on the following word set and the consultation candidate word set after the target candidate word in the consultation candidate word set sequence, updating the candidate word sequence, and splicing the candidate words in the candidate word sequence into a consultation text when the target candidate word is the last candidate word in the candidate word sequence.

Optional, screening out the sharp eye picture group from the eye picture set comprises:
performing graying operation on each eye picture in the eye picture set to acquire a primary eye gray picture set;
selecting each primary eye gray picture in the primary eye gray picture set as a target eye gray picture, and based on the following gray level algorithm, calculating an eye sharpness value of the target eye gray picture:

$$Q = \frac{1}{1 \cdot R}\sum_{i=1}^{I}\sum_{r=1}^{R}\sqrt{\frac{I \cdot R \cdot (G_{(i,r+\epsilon)} + G_{(i,r-\epsilon)} + G_{(i+\epsilon,r)} + G_{(i-\epsilon,r)} - 4G_{(i,r)})^2}{\sum_{i=1}^{I}\sum_{r=1}^{J}(G_{(i,r+\epsilon)} + G_{(i,r-\epsilon)} + G_{(i+\epsilon,r)} + G_{(i-\epsilon,r)} - 4G_{(i,r)})^2}}$$

wherein Q refers to an eye sharpness value, I refers to a picture pixel length of the target eye gray picture, R refers to a picture pixel width of the target eye gray picture, i refers to the i-th pixel along a transverse direction in the target eye gray picture, r refers to the r-th pixel along a longitudinal direction in the target eye gray picture, ϵ refers to a sampling frame length of the gray-level algorithm, G refers to a symbol of gray level, $G_{(i, r)}$ refers to a gray value of a pixel with a coordinate point (i, r) in the target eye gray picture;
determining the eye sharpness value of the target eye gray picture is greater than a preset sharpness threshold;
if not, performing the step of selecting each primary eye gray picture in the primary eye gray picture set as a target eye gray picture;
if yes, adding the target eye gray picture to a preset sharp eye picture group.

Optional, performing primary picture segmentation and size equalization operations on each filtered eye picture in the filtered eye picture group to acquire the standard eyeball picture group comprises:
selecting each filtered eye picture in the filtered eye picture group as a target filtered eye picture, and performing edge erosion operation on the target filtered eye picture to acquire a primary eye edge;
based on watershed algorithm, extracting a primary eyeball edge from the primary eye edge; based on the primary eyeball edge, generating an eyeball mask; and based on the eyeball mask, performing primary segmentation on the target filtered eye picture to acquire a primary eyeball picture;
performing inclination correction and size stretching operations on the primary eyeball picture to acquire a corrected eyeball picture;
generating a gray histogram of the corrected eyeball picture, and by using the gray histogram, performing gray equalization operation on the corrected eyeball picture to acquire a standard eyeball picture and converging all standard eyeball pictures to form a standard eyeball picture group.

Optional, performing secondary picture segmentation operation on the standard eyeball picture group to acquire the eye white picture group, the pupil picture group, and the blood vessel picture group comprises:
selecting each standard eyeball picture in the standard eyeball picture group as a target eyeball picture, performing secondary edge erosion on the target eyeball picture to acquire a secondary eyeball edge picture;
performing circle fitting on the secondary eyeball edge picture to acquire a pupil edge picture;
based on the pupil edge picture, performing picture segmentation on the target eyeball picture to acquire a standard eye white picture and a standard pupil picture;
by using the pupil edge picture, performing masking operation on the secondary eyeball edge picture to acquire a primary blood vessel picture, and performing anisotropic filtering on the primary blood vessel picture to acquire a standard blood vessel picture;
converging all standard eye white pictures to form an eye white picture group, converging all standard pupil pictures to form a pupil picture group, and converging all standard blood vessel pictures to form a blood vessel picture group.

Optional, performing lesion feature analysis on the eye white features, the pupil features and the blood vessel features to acquire an ophthalmologically-observed disease comprises:
identifying eye white disease semantics from the eye white features, identifying pupil disease semantics from the pupil features, and identifying blood vessel disease semantics from the blood vessel features;
converging the eye white disease semantics, the pupil disease semantics and the blood vessel disease semantics to form an eye disease semantics set;

performing feature coding on each eye disease semantics in the eye disease semantics set to acquire disease semantic feature codes;

based on a pre-trained disease analysis model, generating a multi-head disease semantics vector set corresponding to the disease semantics feature codes, and by using a multi-head attention mechanism of the disease analysis model, calculating standard disease semantics vectors corresponding to the multi-head disease semantics vector set;

performing normalization and feature decoding operations on the standard disease semantics vectors in sequence to acquire an ophthalmologically-observed disease.

In order to address the above problem, the present disclosure further provides a neural-network-based-implemented ophthalmologic intelligent consultation apparatus, which includes:

a voice framing module, configured to acquire a consultation voice of a to-be-diagnosed patient, perform correction filtering on the consultation voice to acquire a filtered voice, frame the filtered voice into a consultation voice frame sequence, and extract voice features for the voice frames to acquire a consultation voice feature sequence;

a voice consultation module, configured to perform phoneme recognition on the voice feature sequence to acquire a consultation phoneme sequence, transcode, by a self-attention, the phoneme sequence into a consultation text, perform text segmentation and vectorization operation on the consultation text sequentially to acquire consultation text features, and perform semantics recognition on the consultation text features to acquire an ophthalmologically-described disease;

a picture equalization module, configured to acquire an eye picture set of the to-be-diagnosed patient, screen out a sharp eye picture group from the eye picture set, perform gray-level filtering operation on the sharp eye picture group to acquire a filtered eye picture group, and perform primary picture segmentation and size equalization operations on each filtered eye picture in the filtered eye picture group to acquire a standard eyeball picture group; a feature extracting module, configured to perform secondary picture segmentation operation on the standard eyeball picture group to acquire an eye white picture group, a pupil picture group, and a blood vessel picture group, and extract eye white features from the eye white picture group, pupil features from the pupil picture group and blood vessel features from the blood vessel picture group; and a result generating module, configured to perform lesion feature analysis on the eye white features, the pupil features and the blood vessel features to acquire an ophthalmologically-observed disease, and generate a consultation result based on the ophthalmologically-observed disease and the ophthalmologically-described disease.

In the embodiments of the present disclosure, correction filtering is performed on the consultation voice to acquire a filtered voice, which can reduce noise trend in the consultation voice and retain more voice details; the filtered voice can be framed into a consultation voice frame sequence, which can help perform separate phoneme analysis on each voice frame, and increase the accuracy of the phoneme analysis; voice feature extraction is performed on the voice frames to acquire a consultation voice feature sequence, which can retain multi-dimensional voice features and thus improve the accuracy of the subsequent phoneme analysis; phoneme recognition is performed on the voice feature sequence to acquire a consultation phoneme sequence, and the phoneme sequence is transcoded, by self-attention, into a consultation text, so as to convert the voice into a text and help a computer to perform semantics understanding, thus achieving ophthalmologic disease diagnosis; text segmentation and vectorization operations are performed on the consultation text in sequence to acquire consultation text features, and semantics recognition is performed on the consultation text features to acquire an ophthalmologically-described disease. Based on the descriptive voice of the to-be-diagnosed patient, the disease can be preliminarily determined to improve the accuracy of the ophthalmologic intelligent consultation. An eye picture set of the to-be-patient can be acquired and then a sharp eye picture group can be screened out from the eye picture set to select those eye pictures with more eye detail features for picture processing. Gray-level filtering operation is performed on the sharp eye picture group to acquire a filtered eye picture group, and primary picture segmentation and size equalization operations are performed on each filtered eye picture in the filtered eye picture group to acquire a standard eyeball picture group. In this way, the detail features of the eye pictures can be enhanced while feature comparison can be promoted to improve the accuracy of the feature recognition.

Secondary picture segmentation operation is performed on the standard eyeball picture group to acquire an eye white picture group, a pupil picture group, and a blood vessel picture group, and eye white features are extracted from the eye white picture group, pupil features are extracted from the pupil picture group and blood vessel features are extracted from the blood vessel picture group. Thus, disease analysis can be performed on the eye whites, pupils and the blood vessels so as to ensure the accuracy of the subsequent ophthalmologically-observed disease. Lesion feature analysis is performed on the eye white features, the pupil features and the blood vessel features to acquire an ophthalmologically-observed disease, and a consultation result is generated based on the ophthalmologically-observed disease and the ophthalmologically-described disease. A consultation result can be generated based on the disease ask and answer analysis of the to-be-diagnosed patient and the disease area picture analysis, which therefore avoids the case that the consultation result is obscure due to lack of basic case data or real-time disease data, and further improves the accuracy of the ophthalmologic intelligent consultation. Hence, the neural-network-based-implemented ophthalmologic intelligent consultation method and apparatus of the present disclosure can solve the problem of the low accuracy in the ophthalmologic intelligent consultation.

BRIEF DESCRIPTIONS OF THE DRAWINGS

The implementation of the object, functional features and advantages of the present disclosure will be further described in combination with the embodiments and the accompanying drawings.

DETAILED DESCRIPTIONS OF EMBODIMENTS

It should be understood that the specific embodiments described herein are used only to interpret the present disclosure rather than limit the present disclosure.

One or more embodiments of the present disclosure provide a neural-network-based-implemented ophthalmologic intelligent consultation method. The execution subject of the neural-network-based-implemented ophthalmologic intelligent consultation method may include but not limited to at least one of electronic devices such as a service end, a terminal and the like, which can be configured to perform the method of these embodiments of the present disclosure. In other words, the neural-network-based-implemented ophthalmologic intelligent consultation method can be performed by software or hardware installed on a terminal device or a service end device. The software may be a blockchain platform. The service end includes but not limited to: a single server, a server cluster, a cloud server or a cloud server cluster or the like. The server may be an independent server, or a cloud server capable of providing basic cloud computation services such as cloud service, cloud database, cloud computation, cloud function, cloud storage, network service, cloud communication, middleware service, domain name service, security service, content delivery network (CDN), big data and artificial intelligence platform and the like.

Figure 1:
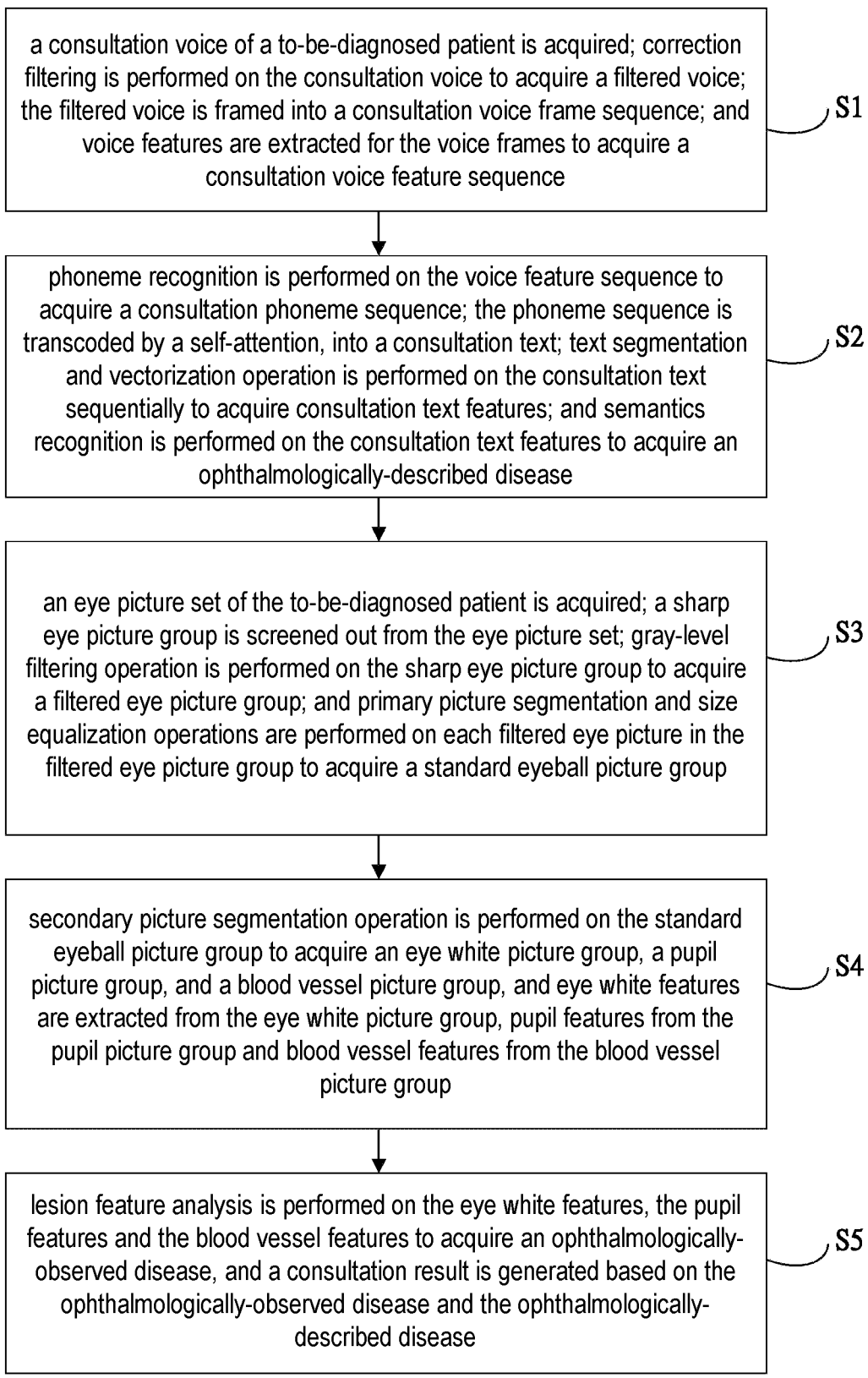
FIG. 1 is a flowchart illustrating a neural-network-based-implemented ophthalmologic intelligent consultation method according to an embodiment of the present disclosure.

As shown in FIG. 1, it is a flowchart illustrating a neural-network-based-implemented ophthalmologic intelligent consultation method according to an embodiment of the present disclosure. In this embodiment, the neural-network-based-implemented ophthalmologic intelligent consultation method includes the following steps.

At step S1, a consultation voice of a to-be-diagnosed patient is acquired; correction filtering is performed on the consultation voice to acquire a filtered voice; the filtered voice is framed into a consultation voice frame sequence; and voice features are extracted for the voice frames to acquire a consultation voice feature sequence.

In one embodiment of the present disclosure, the to-be-diagnosed patient refers to a patient needing to participate in an ophthalmologic intelligent consultation, and the consultation voice refers to an answer voice of the patient who answers the set consultation questions, for example, includes the past medical history and subjective symptoms and the like of the to-be-diagnosed patient.

In one embodiment of the present disclosure, performing correction filtering on the consultation voice to acquire the filtered voice includes:
  performing array signal transformation on the consultation voice to acquire a consultation array signal, and based on the consultation array signal, generating a time sequence of the consultation voice;
  based on the consultation array signal and the time sequence, generating a voice trend term of the consultation voice, and based on the voice trend term, performing voice correction on the consultation array signal to acquire a corrected voice;
  performing denoising and filtering on the corrected voice to acquire a filtered voice.

Specifically, array signal transformation may be performed on the consultation voice by using matlab to acquire the consultation array signal, and a voice time length is extracted from the consultation array signal, and then based on the voice time length and a sampling frequency of the consultation array signal, the time sequence of the consultation voice is calculated.

Specifically, the voice trend term of the consultation voice may be generated based on the consultation array signal and the time sequence by using least square method; voice correction is performed on the consultation array signal based on the voice trend term to acquire a corrected voice, where the corrected voice refers to that the voice trend term in the consultation array signal is deleted. A filtered voice can be acquired by performing denoising and filtering on the corrected voice using a filterDesigner filter.

Specifically, framing the filtered voice into the consultation voice frame sequence includes:
  performing primary framing on the filtered voice based on a preset framing window length to acquire a framed voice sequence;
  based on the following mainlobe windowing algorithm, performing windowing processing on the framed voice sequence to acquire a windowed voice sequence:

$$H(w) = \left\{ 0.5 A(w) + 0.25 \left[ A\left(w - \frac{2\pi}{N-1}\right) + A\left(w + \frac{2\pi}{N-1}\right) \right] \right\} e^{-jw(N-1)/2}$$

wherein $H(w)$ refers to a frequency value of the w-th windowed voice in the windowed voice sequence, $A(w)$ refers to a frequency value of the w-th framed voice in the framed voice sequence, $\pi$ is a symbol of Pi, N refers to a voice window length corresponding to the mainlobe windowing algorithm, e is a symbol of an Euler number, and j is a symbol of an imaginary number;
  calculating an average zero-crossing rate and a short-time voice energy of the windowed voice sequence, and performing endpoint detection on the windowed voice sequence based on the average zero-crossing rate and the short-time voice energy to acquire the consultation voice frame sequence.

In one embodiment of the present disclosure, the windowed voice sequence is acquired by performing windowing processing on the framed voice sequence based on the mainlobe windowing algorithm, and hence, sidelobe voices in the framed voice sequence are cancelled each other such that the voice energy is concentrated on the mainlobes, thus retaining voice feature details.

Specifically, the average zero-crossing rate refers to a number of times that signal crosses a zero value in a short time, and the short-time voice energy refers to change of energy features of the voice signal in a short time.

Figure 2:
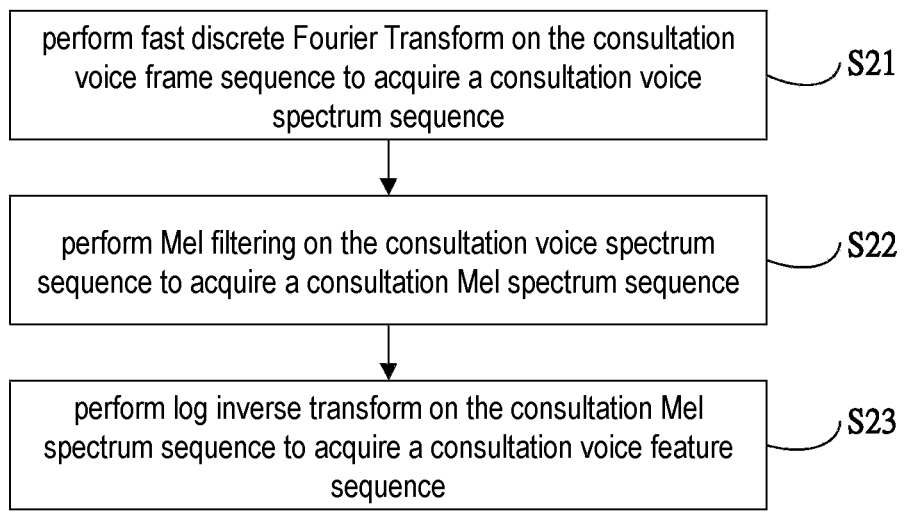
FIG. 2 is a flowchart of extracting a consultation voice feature sequence according to an embodiment of the present disclosure.

Specifically, with reference to FIG. 2, extracting voice features for the voice frames to acquire the consultation voice feature sequence includes:
  at step S21, performing fast discrete Fourier Transform on the consultation voice frame sequence to acquire a consultation voice spectrum sequence;

at step S22, performing Mel filtering on the consultation voice spectrum sequence to acquire a consultation Mel spectrum sequence;

at step S23, performing log inverse transform on the consultation Mel spectrum sequence to acquire a consultation voice feature sequence.

Specifically, the fast Fourier transform (DFT) has the basic idea that the original multi-point sequence is sequentially decomposed into a series of short sequences, and by fully using the symmetry and periodicity of the exponential factor in the calculation formula of the fast Fourier Transform, the fast Fourier transforms corresponding to these short sequences are acquired and properly combined so as to achieve the purpose of deleting repetitive calculations and reducing multiplication operations and simplifying structure.

Specifically, Mel filtering may be performed on the consultation voice spectrum sequence by using Mel filter of MATLAB or python to acquire a consultation Mel spectrum sequence. Log inverse transform may be performed on the consultation Mel spectrum sequence by using Discrete Cosine Transform (DCT) to acquire a consultation voice feature sequence.

In the embodiments of the present disclosure, correction filtering is performed on the consultation voice to acquire a filtered voice, which can reduce noise trend in the consultation voice and retain more voice details; the filtered voice can be framed into a consultation voice frame sequence, which can help perform separate phoneme analysis on each voice frame, and increase the accuracy of the phoneme analysis; voice feature extraction is performed on the voice frames to acquire a consultation voice feature sequence, which can retain multi-dimensional voice features and thus improve the accuracy of the subsequent phoneme analysis.

At step S2, phoneme recognition is performed on the voice feature sequence to acquire a consultation phoneme sequence; the phoneme sequence is transcoded by a self-attention, into a consultation text; text segmentation and vectorization operation is performed on the consultation text sequentially to acquire consultation text features; and semantics recognition is performed on the consultation text features to acquire an ophthalmologically-described disease.

In one embodiment of the present disclosure, performing phoneme recognition on the voice feature sequence to acquire the consultation phoneme sequence includes:

adding position features to the voice feature sequence to acquire voice feature codes;

generating a multi-head voice code vector set of the voice feature codes, and based on self-attention mechanism, calculating morpheme attention features corresponding to the multi-head voice code vector set;

performing attention decoding on the morpheme attention features to acquire a consultation phoneme sequence.

Specifically, the position features refer to position features of the voice features at different positions in the voice feature sequence, and generating the multi-head voice code vector set of the voice feature codes refers to generating query vector, key vector and value vector corresponding to the voice feature codes.

Specifically, based on self-attention mechanism, calculating the morpheme attention features corresponding to the multi-head voice code vector set includes: performing matrix calculation on each vector in the multi-head voice code vector set and performing normalization operation on it to acquire the morpheme attention features; performing attention decoding on the morpheme attention features to acquire the consultation phoneme sequence includes: by using a feed-forward network of multiple positions, a residual network layer and a normalization layer, performing decoding on the morpheme attention features to acquire a consultation phoneme sequence.

In one embodiment of the present disclosure, transcoding, by the self-attention, the phoneme sequence into the consultation text includes:

based on a pre-trained self-attention model, performing primary decoding on the phoneme sequence to acquire a consultation candidate word set sequence;

based on the consultation candidate word set sequence, generating a candidate word sequence, selecting each candidate word in the candidate word sequence as target candidate word, and based on a pre-trained semantics network, generating a following word set corresponding to the target candidate word;

based on the following word set and the consultation candidate word set after the target candidate word in the consultation candidate word set sequence, updating the candidate word sequence, and splicing the candidate words in the candidate word sequence into a consultation text when the target candidate word is the last candidate word in the candidate word sequence.

Specifically, the self-attention model may be a transformer model trained by multiple labeled phoneme training sets, and the semantics network may be a time sequence neural network trained through a huge number of continuous texts.

Specifically, based on the following word set and the consultation candidate word set after the target candidate word in the consultation candidate word set sequence, updating the candidate word sequence includes: fusing the following word set and the consultation candidate word set after the target candidate word in the consultation candidate word set sequence into a standard candidate word set, and selecting a candidate word with the highest correction rate in the standard candidate word set to replace a candidate word after the target candidate word in the candidate word sequence to acquire an updated candidate word sequence.

Specifically, based on the bidirectional maximum matching algorithm, text segmentation is performed on the consultation text to acquire a consultation text word set, and a disused word in the consultation text word set is eliminated to acquire a standard consultation word set. Based on one-hot encoding or word2vec algorithm, vectorization operation is performed on the standard consultation word set to acquire consultation text features.

Specifically, based on a self-attention model trained by using a large number of consultation sentence feature sets subjected to disease labeling, semantics recognition may be performed on the consultation text features to acquire an ophthalmologically-described disease. In one embodiment of the present disclosure, phoneme recognition is performed on the voice feature sequence to acquire a consultation phoneme sequence, and the phoneme sequence is transcoded, by self-attention, into a consultation text, so as to convert the voice into a text and help a computer to perform semantics understanding, thus achieving ophthalmologic disease diagnosis; text segmentation and vectorization operations are performed on the consultation text in sequence to acquire consultation text features, and semantics recognition is performed on the consultation text features to acquire an ophthalmologically-described disease. Based on the descriptive voice of the to-be-diagnosed patient, the disease can be preliminarily determined to improve the accuracy of the ophthalmologic intelligent consultation.

At step S3, an eye picture set of the to-be-diagnosed patient is acquired; a sharp eye picture group is screened out from the eye picture set; gray-level filtering operation is performed on the sharp eye picture group to acquire a filtered eye picture group; and primary picture segmentation and size equalization operations are performed on each filtered eye picture in the filtered eye picture group to acquire a standard eyeball picture group.

In one embodiment of the present disclosure, the eye picture set refers to pictures obtained by photographing the eyes of the to-be-diagnosed patient in close range, and the sharp eye picture group refers to a picture group formed of multiple sharp eye pictures in the eye picture set.

In one embodiment of the present disclosure, screening out the sharp eye picture group from the eye picture set includes:
performing graying operation on each eye picture in the eye picture set to acquire a primary eye gray picture set;
selecting each primary eye gray picture in the primary eye gray picture set as a target eye gray picture, and based on the following gray level algorithm, calculating an eye sharpness value of the target eye gray picture:

$$Q = \frac{1}{1 \cdot R} \sum_{i=1}^{I} \sum_{r=1}^{R} \sqrt{\frac{I \cdot R \cdot (G_{(i,r+\epsilon)} + G_{(i,r-\epsilon)} + G_{(i+\epsilon,r)} + G_{(i-\epsilon,r)} - 4G_{(i,r)})^2}{\sum_{i=1}^{I} \sum_{r=1}^{J} (G_{(i,r+\epsilon)} + G_{(i,r-\epsilon)} + G_{(i+\epsilon,r)} + G_{(i-\epsilon,r)} - 4G_{(i,r)})^2}};$$

wherein Q refers to an eye sharpness value, I refers to a picture pixel length of the target eye gray picture, R refers to a picture pixel width of the target eye gray picture, i refers to the i-th pixel along a transverse direction in the target eye gray picture, r refers to the r-th pixel along a longitudinal direction in the target eye gray picture, $\epsilon$ refers to a sampling frame length of the gray-level algorithm, G refers to a symbol of gray level, $G_{(i,r)}$ refers to a gray value of a pixel with a coordinate point (i, r) in the target eye gray picture;
determining the eye sharpness value of the target eye gray picture is greater than a preset sharpness threshold;
if not, performing the step of selecting each primary eye gray picture in the primary eye gray picture set as a target eye gray picture;
if yes, adding the target eye gray picture to a preset sharp eye picture group.

In one embodiment of the present disclosure, when the eye sharpness value of the target eye gray picture is calculated based on the gray level algorithm, the entire sharpness of the target eye gray picture can be determined based on the amplitude value of the gray change in each region in the target eye gray picture, so as to increase the accuracy of the sharpness calculation.

Specifically, based on Gaussian filtering algorithm or median filtering algorithm, gray-level filtering operation may be performed on the sharp eye picture group to acquire a filtered eye picture group.

Figure 3:
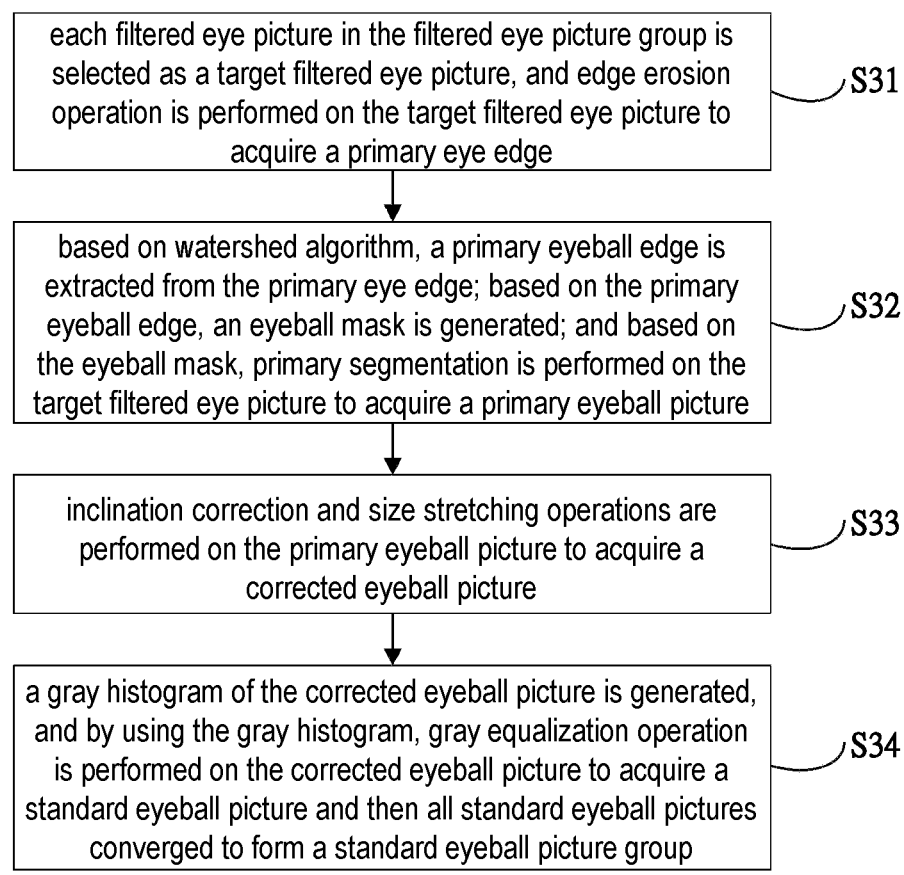
FIG. 3 is a flowchart of generating a standard eyeball picture group according to an embodiment of the present disclosure.

Specifically, as shown in FIG. 3, performing primary picture segmentation and size equalization operations on each filtered eye picture in the filtered eye picture group to acquire the standard eyeball picture group includes the following steps.

At step S31, each filtered eye picture in the filtered eye picture group is selected as a target filtered eye picture, and edge erosion operation is performed on the target filtered eye picture to acquire a primary eye edge.

At step S32, based on watershed algorithm, a primary eyeball edge is extracted from the primary eye edge; based on the primary eyeball edge, an eyeball mask is generated; and based on the eyeball mask, primary segmentation is performed on the target filtered eye picture to acquire a primary eyeball picture.

At step S33, inclination correction and size stretching operations are performed on the primary eyeball picture to acquire a corrected eyeball picture.

At step S34, a gray histogram of the corrected eyeball picture is generated, and by using the gray histogram, gray equalization operation is performed on the corrected eyeball picture to acquire a standard eyeball picture and then all standard eyeball pictures converged to form a standard eyeball picture group.

In one embodiment of the present disclosure, edge erosion operation may be performed on the target filtered eye picture by using canny operator or sobel operator to acquire a primary eye edge; by using hough algorithm, inclination correction is performed on the primary eyeball picture, where the size stretching refers to enlarging the picture size of the primary eyeball picture to a preset picture size pro rata.

In one embodiment of the present disclosure, an eye picture set of the to-be-patient can be acquired and then a sharp eye picture group can be screened out from the eye picture set to select those eye pictures with more eye detail features for picture processing. Gray-level filtering operation is performed on the sharp eye picture group to acquire a filtered eye picture group, and primary picture segmentation and size equalization operations are performed on each filtered eye picture in the filtered eye picture group to acquire a standard eyeball picture group. In this way, the detail features of the eye pictures can be enhanced while feature comparison can be promoted to improve the accuracy of the feature recognition.

At step S4, secondary picture segmentation operation is performed on the standard eyeball picture group to acquire an eye white picture group, a pupil picture group, and a blood vessel picture group, and eye white features are extracted from the eye white picture group, pupil features from the pupil picture group and blood vessel features from the blood vessel picture group.

In one embodiment of the present disclosure, performing secondary picture segmentation operation on the standard eyeball picture group to acquire the eye white picture group, the pupil picture group, and the blood vessel picture group includes:
selecting each standard eyeball picture in the standard eyeball picture group as a target eyeball picture, performing secondary edge erosion on the target eyeball picture to acquire a secondary eyeball edge picture;
performing circle fitting on the secondary eyeball edge picture to acquire a pupil edge picture;
based on the pupil edge picture, performing picture segmentation on the target eyeball picture to acquire a standard eye white picture and a standard pupil picture;
by using the pupil edge picture, performing masking operation on the secondary eyeball edge picture to acquire a primary blood vessel picture, and performing anisotropic filtering on the primary blood vessel picture to acquire a standard blood vessel picture;
converging all standard eye white pictures to form an eye white picture group, converging all standard pupil pictures to form a pupil picture group, and converging all standard blood vessel pictures to form a blood vessel picture group.

Specifically, the method of performing secondary edge erosion on the target eyeball picture to acquire the secondary eyeball edge picture is the same as the method of performing edge erosion operation on the target filtered eye picture to acquire the primary eye edge in the step S3 and will not be repeated herein.

Specifically, circle fitting may be performed on the secondary eyeball edge picture based on least square method to acquire the pupil edge picture, where the anisotropic filtering (AF) may associate and filter the factors such as a texture feature and a picture angle and the like to retain more texture features.

Specifically, extracting the eye white features from the eye white picture group, the pupil features from the pupil picture group and the blood vessel features from the blood vessel picture group include: by using a pre-trained convolutional neural network, performing feature dimension reduction on each eye white picture in the eye white picture group, performing feature dimension reduction on each pupil picture in the pupil picture group, and performing feature dimension reduction on each blood vessel picture in the blood vessel picture group, so as to facilitate subsequent feature recognition and computation dimension reduction.

In one embodiment of the present disclosure, secondary picture segmentation operation is performed on the standard eyeball picture group to acquire the eye white picture group, the pupil picture group and the blood vessel picture group, and then the eye white features are extracted from the eye white picture group, the pupil features from the pupil picture group and the blood vessel features from the blood vessel picture group. In this way, disease analysis may be performed on the eye whites, the pupils and the blood vessels to ensure the accuracy of subsequent ophthalmologically-observed disease.

At step S5, lesion feature analysis is performed on the eye white features, the pupil features and the blood vessel features to acquire an ophthalmologically-observed disease, and a consultation result is generated based on the ophthalmologically-observed disease and the ophthalmologically-described disease.

In one embodiment of the present disclosure, performing lesion feature analysis on the eye white features, the pupil features and the blood vessel features to acquire the ophthalmologically-observed disease includes:

identifying eye white disease semantics from the eye white features, identifying pupil disease semantics from the pupil features, and identifying blood vessel disease semantics from the blood vessel features;

converging the eye white disease semantics, the pupil disease semantics and the blood vessel disease semantics to form an eye disease semantics set;

performing feature coding on each eye disease semantics in the eye disease semantics set to acquire disease semantic feature codes;

based on a pre-trained disease analysis model, generating a multi-head disease semantics vector set corresponding to the disease semantics feature codes, and by using a multi-head attention mechanism of the disease analysis model, calculating standard disease semantics vectors corresponding to the multi-head disease semantics vector set; and, performing normalization and feature decoding operations on the standard disease semantics vectors in sequence to acquire an ophthalmologically-observed disease.

Specifically, the disease analysis model may be a support vector machine model trained by a large number of labeled disease semantics. The ophthalmologically-observed disease can be acquired by performing normalization on the standard disease semantics vectors using softmax function and performing feature decoding operation on the standard disease semantics vectors using a multilayer perceptron.

Specifically, generating the consultation result based on the ophthalmologically-observed disease and the ophthalmologically-described disease includes: generating an observed disease result based on the ophthalmologically-observed disease and the standard eyeball picture group, and generating a described-disease result based on the ophthalmologically-described disease and the consultation text, and splicing the observed disease result and the described-disease result into a consultation result which can be fed back to the ophthalmologist, helping the ophthalmologist to determine the disease.

In one embodiment of the present disclosure, when lesion feature analysis is performed on the eye white features, the pupil features and the blood vessel features to acquire the ophthalmologically-observed disease and the consultation result is generated based on the ophthalmologically-observed disease and the ophthalmologically-described disease, the consultation result can be generated based on the disease ask and answer analysis and the disease area picture analysis of the to-be-diagnosed patient, which thus avoids the case that the consultation result is obscure due to lack of basic case data or real-time disease data, and further improves the accuracy of the ophthalmologic intelligent consultation.

In the embodiments of the present disclosure, correction filtering is performed on the consultation voice to acquire a filtered voice, which can reduce noise trend in the consultation voice and retain more voice details; the filtered voice can be framed into a consultation voice frame sequence, which can help perform separate phoneme analysis on each voice frame, and increase the accuracy of the phoneme analysis; voice feature extraction is performed on the voice frames to acquire a consultation voice feature sequence, which can retain multi-dimensional voice features and thus improve the accuracy of the subsequent phoneme analysis; phoneme recognition is performed on the voice feature sequence to acquire a consultation phoneme sequence, and the phoneme sequence is transcoded, by self-attention, into a consultation text, so as to convert the voice into a text and help a computer to perform semantics understanding, thus achieving ophthalmologic disease diagnosis; text segmentation and vectorization operations are performed on the consultation text in sequence to acquire consultation text features, and semantics recognition is performed on the consultation text features to acquire an ophthalmologically-described disease. Based on the descriptive voice of the to-be-diagnosed patient, the disease can be preliminarily determined to improve the accuracy of the ophthalmologic intelligent consultation. An eye picture set of the to-be-patient can be acquired and then a sharp eye picture group can be screened out from the eye picture set to select those eye pictures with more eye detail features for picture processing. Gray-level filtering operation is performed on the sharp eye picture group to acquire a filtered eye picture group, and primary picture segmentation and size equalization operations are performed on each filtered eye picture in the filtered eye picture group to acquire a standard eyeball picture group. In this way, the detail features of the eye pictures can be enhanced while feature comparison can be promoted to improve the accuracy of the feature recognition.

Secondary picture segmentation operation is performed on the standard eyeball picture group to acquire an eye white picture group, a pupil picture group, and a blood vessel picture group, and eye white features are extracted from the eye white picture group, pupil features are extracted from the pupil picture group and blood vessel features are extracted from the blood vessel picture group. Thus, disease analysis can be performed on the eye whites, pupils and the blood vessels so as to ensure the accuracy of the subsequent ophthalmologically-observed disease. Lesion feature analysis is performed on the eye white features, the pupil features and the blood vessel features to acquire an ophthalmologically-observed disease, and a consultation result is generated based on the ophthalmologically-observed disease and the ophthalmologically-described disease. A consultation result can be generated based on the disease ask and answer analysis of the to-be-diagnosed patient and the disease area picture analysis, which therefore avoids the case that the consultation result is obscure due to lack of basic case data or real-time disease data, and further improves the accuracy of the ophthalmologic intelligent consultation. Hence, the neural-network-based-implemented ophthalmologic intelligent consultation method of the present disclosure can solve the problem of the low accuracy in the ophthalmologic intelligent consultation.

Figure 4:
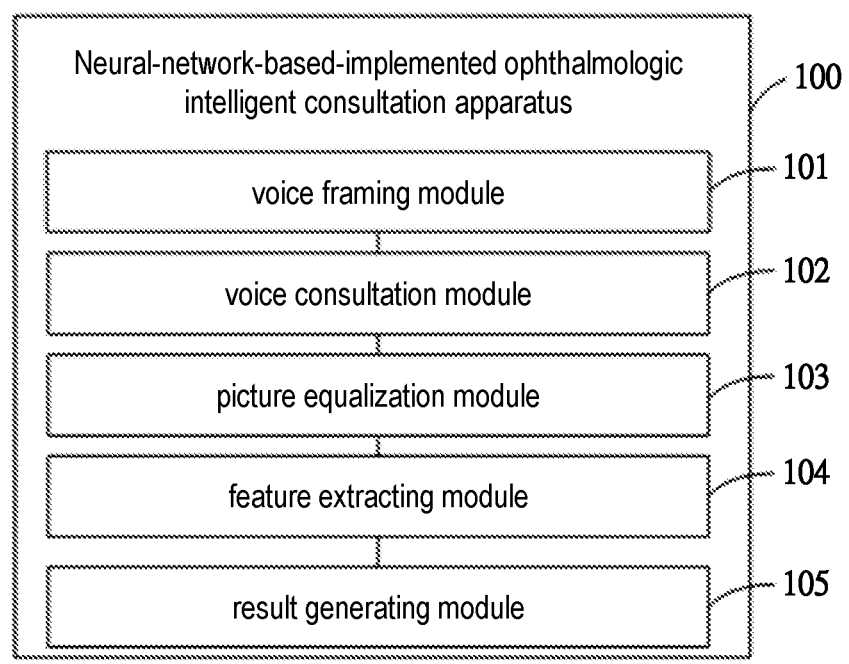
FIG. 4 is a functional module diagram illustrating a neural-network-based-implemented ophthalmologic intelligent consultation apparatus according to an embodiment of the present disclosure.

As shown in FIG. 4, it is a functional module diagram illustrating a neural-network-based-implemented ophthalmologic intelligent consultation apparatus according to an embodiment of the present disclosure.

The neural-network-based-implemented ophthalmologic intelligent consultation apparatus 100 can perform the above neural-network-based-implemented ophthalmologic intelligent consultation method. Further, the neural-network-based-implemented ophthalmologic intelligent consultation apparatus 100 can be installed in an electronic device. Based on the implemented functions, the neural-network-based-implemented ophthalmologic intelligent consultation apparatus 100 may include a voice framing module 101, a voice consultation module 102, a picture equalization module 103, a feature extracting module 104 and a result generating module 105. The module in the present disclosure may also be referred to as unit, which is a series of computer program fragments stored in the memory of the electronic device and executed by the processor of the electronic device to perform fixed functions.

In this embodiment, the modules/units have the following functions.

The voice framing module 101 is configured to acquire a consultation voice of a to-be-diagnosed patient, perform correction filtering on the consultation voice to acquire a filtered voice, frame the filtered voice into a consultation voice frame sequence, and extract voice features for the voice frames to acquire a consultation voice feature sequence; where framing the filtered voice into the consultation voice frame sequence includes: performing primary framing on the filtered voice based on a preset framing window length to acquire a framed voice sequence; based on the following mainlobe windowing algorithm, performing windowing processing on the framed voice sequence to acquire a windowed voice sequence:

$$H(w) = \left\{ 0.5A(w) + 0.25\left[A\left(w - \frac{2\pi}{N-1}\right) + A\left(w + \frac{2\pi}{N-1}\right)\right]\right\} e^{-jw(N-1)/2};$$

wherein H(w) refers to a frequency value of the w-th windowed voice in the windowed voice sequence, A(w) refers to a frequency value of the w-th framed voice in the framed voice sequence, π is a symbol of Pi, N refers to a voice window length corresponding to the mainlobe windowing algorithm, e is a symbol of an Euler number, and j is a symbol of an imaginary number; calculating an average zero-crossing rate and a short-time voice energy of the windowed voice sequence, and performing endpoint detection on the windowed voice sequence based on the average zero-crossing rate and the short-time voice energy to acquire the consultation voice frame sequence;

the voice consultation module 102 is configured to perform phoneme recognition on the voice feature sequence to acquire a consultation phoneme sequence, transcode, by a self-attention, the phoneme sequence into a consultation text, perform text segmentation and vectorization operation on the consultation text sequentially to acquire consultation text features, and perform semantic recognition on the consultation text features to acquire an ophthalmologically-described disease;

the picture equalization module 103 is configured to acquire an eye picture set of the to-be-diagnosed patient, screen out a sharp eye picture group from the eye picture set, perform gray-level filtering operation on the sharp eye picture group to acquire a filtered eye picture group, and perform primary picture segmentation and size equalization operations on each filtered eye picture in the filtered eye picture group to acquire a standard eyeball picture group;

the feature extracting module 104 is configured to perform secondary picture segmentation operation on the standard eyeball picture group to acquire an eye white picture group, a pupil picture group, and a blood vessel picture group, and extract eye white features from the eye white picture group, pupil features from the pupil picture group and blood vessel features from the blood vessel picture group; and the result extracting module 105 is configured to perform lesion feature analysis on the eye white features, the pupil features and the blood vessel features to acquire an ophthalmologically-observed disease, and generate a consultation result based on the ophthalmologically-observed disease and the ophthalmologically-described disease.

Specifically, in the embodiments of the present disclosure, the modules in the neural-network-based-implemented ophthalmologic intelligent consultation apparatus 100 can employ the same technical means as the neural-network-based-implemented ophthalmologic intelligent consultation method shown in FIGS. 1 to 3 and thus can generate the same technical effect and therefore will not be repeated herein.

It is finally noted that the above embodiments are used only to illustrate the technical solutions of the present disclosure rather than to limit the present disclosure. Although the present disclosure is detailed by referring to the preferred embodiments, those skilled in the art should understand that any changes or equivalent substitutions can be made to the technical solutions of the present disclosure within the spirit and scope of the technical solutions of the present disclosure.

What is claimed is:

1. A neural-network-based-implemented ophthalmologic intelligent consultation method, comprising:

at step S1, acquiring a consultation voice of a to-be-diagnosed patient, performing correction filtering on the consultation voice to acquire a filtered voice, framing the filtered voice into a consultation voice frame sequence, and extracting voice features for the voice frames to acquire a consultation voice feature sequence, wherein framing the filtered voice into the consultation voice frame sequence comprises:

at step S11, performing primary framing on the filtered voice based on a preset framing window length to acquire a framed voice sequence;

at step S12, performing windowing processing on the framed voice sequence to acquire a windowed voice sequence based on the following mainlobe windowing algorithm:

$$H(w) = \left\{ 0.5A(w) + 0.25\left[ A\left(w - \frac{2\pi}{N-1}\right) + A\left(w + \frac{2\pi}{N-1}\right) \right] \right\} e^{-jw(N-1)/2}$$

wherein H(w) refers to a frequency value of the w-th windowed voice in the windowed voice sequence, A(w) refers to a frequency value of the w-th framed voice in the framed voice sequence, $\pi$ is a symbol of Pi, N refers to a voice window length corresponding to the mainlobe windowing algorithm, e is a symbol of an Euler number, and j is a symbol of an imaginary number; and at step S13, calculating an average zero-crossing rate and a short-time voice energy of the windowed voice sequence, and performing endpoint detection on the windowed voice sequence based on the average zero-crossing rate and the short-time voice energy to acquire the consultation voice frame sequence;

at step S2, performing phoneme recognition on the voice feature sequence to acquire a consultation phoneme sequence, transcoding, by a self-attention, the phoneme sequence into a consultation text, performing text segmentation and vectorization operation on the consultation text sequentially to acquire consultation text features, and performing semantics recognition on the consultation text features to acquire an ophthalmologically-described disease;

at step S3, acquiring an eye picture set of the to-be-diagnosed patient, screening out a sharp eye picture group from the eye picture set, performing gray-level filtering operation on the sharp eye picture group to acquire a filtered eye picture group, and performing primary picture segmentation and size equalization operations on each filtered eye picture in the filtered eye picture group to acquire a standard eyeball picture group;

at step S4, performing secondary picture segmentation operation on the standard eyeball picture group to acquire an eye white picture group, a pupil picture group, and a blood vessel picture group, and extracting eye white features from the eye white picture group, pupil features from the pupil picture group and blood vessel features from the blood vessel picture group; and at step S5, performing lesion feature analysis on the eye white features, the pupil features and the blood vessel features to acquire an ophthalmologically-observed disease, and generating a consultation result based on the ophthalmologically-observed disease and the ophthalmologically-described disease;

wherein performing lesion feature analysis on the eye white features, the pupil features and the blood vessel features to acquire an ophthalmologically-observed disease comprises:

identifying eye white disease semantics from the eye white features, identifying pupil disease semantics from the pupil features, and identifying blood vessel disease semantics from the blood vessel features;

converging the eye white disease semantics, the pupil disease semantics and the blood vessel disease semantics to form an eye disease semantics set;

performing feature coding on each eye disease semantics in the eye disease semantics set to acquire disease semantic feature codes;

generating a multi-head disease semantics vector set corresponding to the disease semantics feature codes based on a pre-trained disease analysis model, and calculating standard disease semantics vectors corresponding to the multi-head disease semantics vector set through a multi-head attention mechanism of the disease analysis model; and performing normalization and feature decoding operations on the standard disease semantics vectors in sequence to acquire an ophthalmologically-observed disease;

wherein the disease analysis model is a support vector machine model trained by a large number of labeled disease semantics, the ophthalmologically-observed disease can be acquired by performing normalization on the standard disease semantics vectors using softmax function and performing feature decoding operation on the standard disease semantics vectors using a multilayer perceptron;

wherein generating the consultation result based on the ophthalmologically-observed disease and the ophthalmologically-described disease includes: generating an observed disease result based on the ophthalmologically-observed disease and the standard eyeball picture group, and generating a described-disease result based on the ophthalmologically-described disease and the consultation text, and splicing the observed disease result and the described-disease result into a consultation result.

2. The ophthalmologic intelligent consultation method of claim 1, wherein the performing correction filtering on the consultation voice to acquire the filtered voice comprises:

performing array signal transformation on the consultation voice to acquire a consultation array signal, and generating a time sequence of the consultation voice based on the consultation array signal;

generating a voice trend term of the consultation voice based on the consultation array signal and the time sequence, and performing voice correction on the consultation array signal to acquire a corrected voice based on the voice trend term; and performing denoising and filtering on the corrected voice to acquire a filtered voice.

3. The ophthalmologic intelligent consultation method of claim 1, wherein the extracting voice features for the voice frames to acquire a consultation voice feature sequence comprises:

performing fast discrete Fourier Transform on the consultation voice feature sequence to acquire a consultation voice spectrum sequence;

performing Mel filtering on the consultation voice spectrum sequence to acquire a consultation Mel spectrum sequence; and performing log inverse transform on the consultation Mel spectrum sequence to acquire a consultation voice feature sequence.

4. The ophthalmologic intelligent consultation method of claim 1, wherein performing phoneme recognition on the voice feature sequence to acquire the consultation phoneme sequence comprises:

adding position features to the voice feature sequence to acquire voice feature codes;

generating a multi-head voice code vector set of the voice feature codes, and calculating morpheme attention features corresponding to the multi-head voice code vector set based on self-attention mechanism; and performing attention decoding on the morpheme attention features to acquire a consultation phoneme sequence.

5. The ophthalmologic intelligent consultation method of claim 1, wherein the transcoding, by the self-attention, the phoneme sequence into the consultation text comprises:

performing primary decoding on the phoneme sequence to acquire a consultation candidate word set sequence based on a pre-trained self-attention model;

generating a candidate word sequence, selecting each candidate word in the candidate word sequence as target candidate word based on the consultation candidate word set sequence, and generating a following word set corresponding to the target candidate word based on a pre-trained semantics network; and updating the candidate word sequence based on the following word set and the consultation candidate word set after the target candidate word in the consultation candidate word set sequence, and splicing the candidate words in the candidate word sequence into a consultation text in response to the target candidate word is the last candidate word in the candidate word sequence.

6. The ophthalmologic intelligent consultation method of claim 1, wherein the screening out the sharp eye picture group from the eye picture set comprises:

performing graying operation on each eye picture in the eye picture set to acquire a primary eye gray picture set;

selecting each primary eye gray picture in the primary eye gray picture set as a target eye gray picture, and calculating an eye sharpness value of the target eye gray picture based on the following gray level algorithm:

$$Q = \frac{1}{1 \cdot R} \sum_{i=1}^{I} \sum_{r=1}^{R} \sqrt{\frac{I \cdot R \cdot (G_{(i,r+\epsilon)} + G_{(i,r-\epsilon)} + G_{(i+\epsilon,r)} + G_{(i-\epsilon,r)} - 4G_{(i,r)})^2}{\sum_{i=1}^{I} \sum_{r=1}^{J} (G_{(i,r+\epsilon)} + G_{(i,r-\epsilon)} + G_{(i+\epsilon,r)} + G_{(i-\epsilon,r)} - 4G_{(i,r)})^2}};$$

wherein Q refers to an eye sharpness value, I refers to a picture pixel length of the target eye gray picture, R refers to a picture pixel width of the target eye gray picture, i refers to the i-th pixel along a transverse direction in the target eye gray picture, r refers to the r-th pixel along a longitudinal direction in the target eye gray picture, F refers to a sampling frame length of the gray-level algorithm, G refers to a symbol of gray level, $G_{(i, r)}$ refers to a gray value of a pixel with a coordinate point (i, r) in the target eye gray picture;

determining the eye sharpness value of the target eye gray picture is greater than a preset sharpness threshold;

performing the step of selecting each primary eye gray picture in the primary eye gray picture set as a target eye gray picture in response to the eye sharpness value of the target eye gray picture is not greater than a preset sharpness threshold; and adding the target eye gray picture to a preset sharp eye picture group in response to the eye sharpness value of the target eye gray picture is greater than a preset sharpness threshold.

7. The ophthalmologic intelligent consultation method of claim 1, wherein the performing primary picture segmentation and size equalization operations on each filtered eye picture in the filtered eye picture group to acquire the standard eyeball picture group comprises:

selecting each filtered eye picture in the filtered eye picture group as a target filtered eye picture, and performing edge erosion operation on the target filtered eye picture to acquire a primary eye edge;

extracting a primary eyeball edge from the primary eye edge based on watershed algorithm, generating an eyeball mask based on the primary eyeball edge, and performing primary segmentation on the target filtered eye picture to acquire a primary eyeball picture based on the eyeball mask;

performing inclination correction and size stretching operations on the primary eyeball picture to acquire a corrected eyeball picture; and generating a gray histogram of the corrected eyeball picture, and performing gray equalization operation on the corrected eyeball picture through the gray histogram to acquire a standard eyeball picture and converging all standard eyeball pictures to form a standard eyeball picture group.

8. The ophthalmologic intelligent consultation method of claim 1, wherein performing secondary picture segmentation operation on the standard eyeball picture group to acquire the eye white picture group, the pupil picture group, and the blood vessel picture group comprises:

selecting each standard eyeball picture in the standard eyeball picture group as a target eyeball picture, performing secondary edge erosion on the target eyeball picture to acquire a secondary eyeball edge picture;

performing circle fitting on the secondary eyeball edge picture to acquire a pupil edge picture;

performing picture segmentation on the target eyeball picture based on the pupil edge picture to acquire a standard eye white picture and a standard pupil picture;

performing masking operation on the secondary eyeball edge picture through the pupil edge picture to acquire a primary blood vessel picture, and performing anisotropic filtering on the primary blood vessel picture to acquire a standard blood vessel picture; and converging all standard eye white pictures to form an eye white picture group, converging all standard pupil pictures to form a pupil picture group, and converging all standard blood vessel pictures to form a blood vessel picture group.

9. A consultation apparatus for implementing the ophthalmologic intelligent consultation method according to claim 1, comprising:

a voice framing module, configured to acquire a consultation voice of a to-be-diagnosed patient, perform correction filtering on the consultation voice to acquire a filtered voice, frame the filtered voice into a consultation voice frame sequence, and extract voice features for the voice frames to acquire a consultation voice feature sequence;
a voice consultation module, configured to perform phoneme recognition on the voice feature sequence to acquire a consultation phoneme sequence, transcode, by a self-attention, the phoneme sequence into a consultation text, perform text segmentation and vectorization operation on the consultation text sequentially to acquire consultation text features, and perform semantics recognition on the consultation text features to acquire an ophthalmologically-described disease;
a picture equalization module, configured to acquire an eye picture set of the to-be-diagnosed patient, screen out a sharp eye picture group from the eye picture set, perform gray-level filtering operation on the sharp eye picture group to acquire a filtered eye picture group, and perform primary picture segmentation and size equalization operations on each filtered eye picture in the filtered eye picture group to acquire a standard eyeball picture group;
a feature extracting module, configured to perform secondary picture segmentation operation on the standard eyeball picture group to acquire an eye white picture group, a pupil picture group, and a blood vessel picture group, and extract eye white features from the eye white picture group, pupil features from the pupil picture group and blood vessel features from the blood vessel picture group; and
a result generating module, configured to perform lesion feature analysis on the eye white features, the pupil features and the blood vessel features to acquire an ophthalmologically-observed disease, and generate a consultation result based on the ophthalmologically-observed disease and the ophthalmologically-described disease.

* * * * *